| United States Patent [19] | [11] 4,055,186 |
|---|---|
| Leveen | [45] Oct. 25, 1977 |

[54] ANASTOMOSIS BUTTON

[76] Inventor: Harry H. Leveen, 800 Poly Place, Brooklyn, N.Y. 11209

[21] Appl. No.: 657,205

[22] Filed: Feb. 11, 1976

[51] Int. Cl.² .............................................. A61B 17/04
[52] U.S. Cl. ................................................. 128/334 C
[58] Field of Search ........................ 128/334 R, 334 C

[56] References Cited

U.S. PATENT DOCUMENTS

| 3,771,526 | 11/1973 | Rudie | 128/334 C |
| 3,974,835 | 8/1976 | Hardy, Jr. | 128/334 C |

FOREIGN PATENT DOCUMENTS

| 357,306 | 8/1922 | Germany | 128/334 C |

OTHER PUBLICATIONS

Narter et al., "An Experimental Method of Nonsuture Anastomosis of the Aorta", IN Surgery, Gynecology and Obstetrics 119²:362–364, 1964.

*Primary Examiner*—Channing L. Pace
*Attorney, Agent, or Firm*—Brooks, Haidt, Haffner & Delahunty

[57] ABSTRACT

An anastomosis button formed of a pair of axially engaged complementary clamping members, each clamping member includes a hub and a crown. The crown includes a clamping collar which is coaxially positioned about and spaced outwardly of the hub medially along the length of the hub and a plurality of spring leaves which are spaced apart and attached at one set of ends to the hub and at the other set of ends to the clamping collar.

6 Claims, 8 Drawing Figures

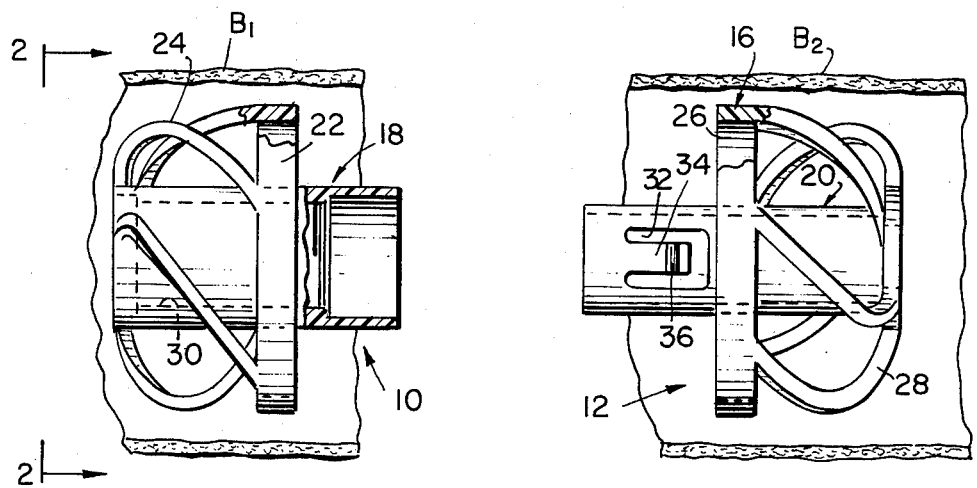
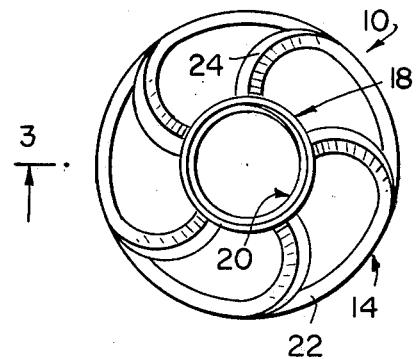
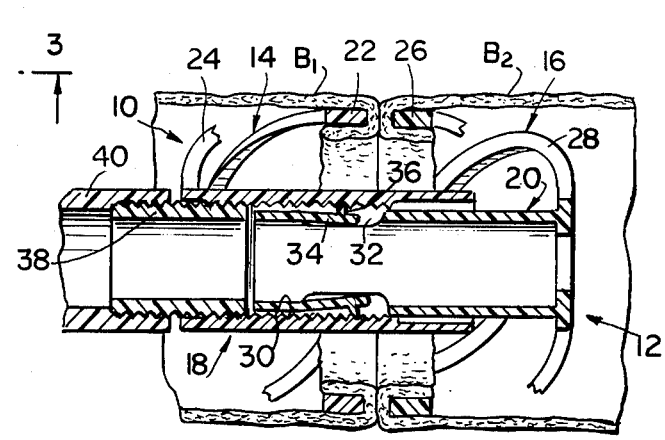
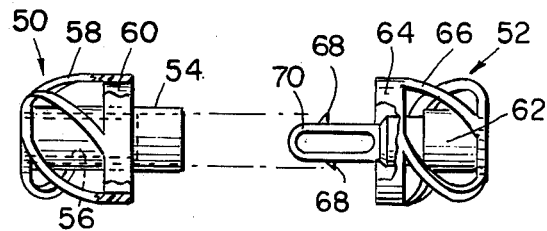

ANASTOMOSIS BUTTON

This invention relates to anastomosis of the bowel and in particular provides a new anastomosis button construction.

It is frequently necessary during the course of surgery to remove a segment of the intestines. When this is done, the opened ends of remaining bowel must be joined so that intestinal continuity is reestablished This is best accomplished by an inverting type of anastomosis. In this type of anastomosis, the serosa of the bowel is turned inward so that the contact of the two pieces of bowel is established on their outer, i.e., serosal, surface. The anastomosis is said to be serosa to serosa. Although this anastomosis can be accomplished by suture, it would be quicker and easier if some form of intenstinal prosthesis were available to hold the joined edges together.

John B. Murphy first devised an appliance (anastomosis button) which could be inserted into the lumen of the bowel to hold the edges in proximity while healing occurred. (Murphy, J.B., Cholecysto-intestinal, gastrointenstinal, entero-intestinal anastomosis and approximation without sutures. The Chicago Medical Recorder 3:803-840 1892). Subsequent experience with Murphy's device disclosed that the device was occasionally retained because the compression which the device was supposed to exert on the tissue was insufficient to bring about necrosis. The release of the device did not occur without necrosis of the spur that was holding it, therefore, it did not pass out of the intestinal tract. Also Murphy's device had only a small central lumen and occasionally intestinal obstruction resulted. For these reasons, the device was largely abandoned although some have continued its use in low rectal anastomosis after colonic resection.

It is thus a primary object of this invention to provide an anastomosis button which will obviate these difficulties.

An investigation was made as to the mechanism of intestinal obstruction produced by intraluminal objects. Intraluminal objects of large diameter would pass through the intestinal tract without producing intestinal obstruction providing that the object was permiable to gas and fluid. If fluid and gas were unable to pass though the intraluminal object, the proximal bowel was dilated by an accumulation of gas and liquid. This dilation obliterated the propulsive force of intestinal peristalsis, and resulted in intestinal obstruction with failure of the object to pass. The ideal device should be of simple construction and the design must be of an open mesh work to avoid intestinal obstruction.

In accordance with this invention an anastomosis button is formed of a pair of axially engaged complementary clamping members. Each clamping member includes an integral hub and crown in which the hub axially mates and engages the complementary hub on the other clamping member. The crown includes a clamping collar which is coaxially positioned about and spaced outwardly of the hub medially along the length of the hub and a plurality of spring leaves which are spaced apart and attached at one set of ends to the hub and at the other set of ends to the clamping collar. Preferably the leaves are spiral in form. The two clamping members are brought together with two pieces of bowel to be joined in a conventional manner positioned over the clamping members and around the confronting edges of the clamping collars as the clamping members are axially engaged. The spacing of the clamping collars outwardly of the hubs is obstructed only by the hubs and spring leaves such that passage of fluids and gases through the bowel is relatively unobstructed. At the same time the spring leaves which are spaced at arcuate intervals about the hub and collar apply even pressure under slight compression to hold the clamping collars together with the bowel between them until agglutination takes place.

When utilized for intraluminal anastomosis of the intestines, the device of this invention has the following advantages: It is rapid. No intraluminal spur results as in sutured anastomosis from turning in too much bowel. The anastomotic site appears almost identical to the adjacent bowel, and the union cannot be visualized on gross inspection of thw bowel.

The device of this invention is preferably manufactured of synthetic thermoplastic material and is of unitary design making it possible to injection mold the two pieces. The axial engagement of the hubs is preferably rotationally disengageable such that after the two pieces are engaged by pushing them together, the two pieces can be disengaged only by screwing them apart. Preferably, a ratchet on one piece operates on a conventional screw thread on the other, as in the original Murphy button.

The integral compression spring leaves are molded into the stucture of the device so that adequate compression is maintained at all times on the two opposing pieces of bowel which insures that the septum being compressed will pinch itself off and release the internal device for passage down the intenstinal tract. The device thus preferably utilizes an open spiral lattice spring which is easily compressed and makes appropriate pressure on the bowel septum which is compressed between the two members. This open lattice work spring offers no solid obstruction to the passage of fluid and gas through the intestinal lumen. The device can be constructed of a plastic which is softened by the intenstinal ferments, although this is not an essential factor since a device constructed of rigid plastic readily passes through the intestinal tract.

For a more complete understanding of the practical application of this invention, reference is made to the appended drawings in which:

FIG. 1 is an enlarged, partially sectioned view of a portion of the bowel showing the two parts of an anastomosis button in accordance with this invention as they are initially positioned in the cut confronting portions of the bowel;

FIG. 2 is an end view of the portion of the device of this invention as seen from line 2—2 in FIG. 1;

FIG. 3 is a section taken along line 3—3 in FIG. 2 after the device of the invention has been pushed together to hold the cut ends of bowel with their serosal surfaces in contact;

FIG. 4 is a view of another device in accordance with this invention which is particularly suitable in joining small bowel portions;

Figure 5:
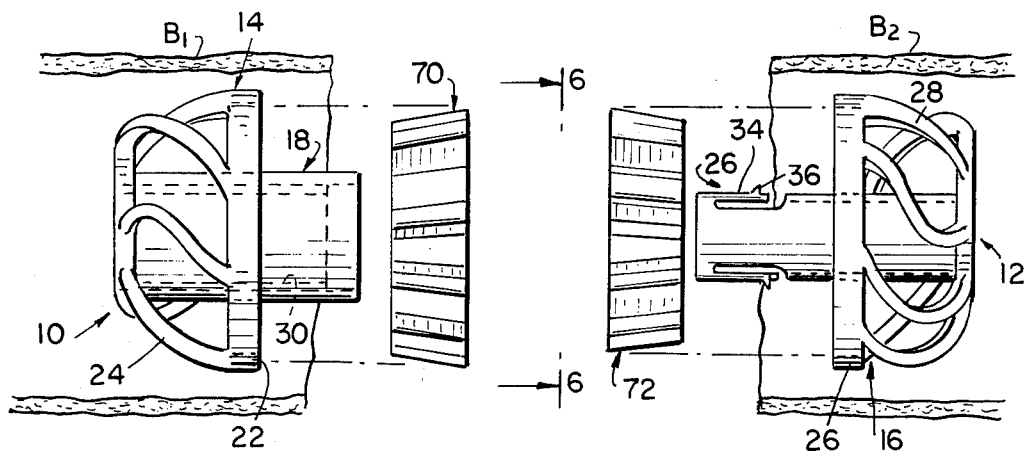
FIG. 5 is a view similar to FIG. 1 illustrating a device useful in conjunction with the anastomosis button, particularly in bowels of large diameter for aiding in securing the cut ends of the bowel about the anastomosis button parts.

Referring particularly to FIGS. 1-3, an anastomosis button in accordance with the present invention consists of two separate, integrally molded clamping members 10 and 12. Each clamping member 10 and 12 basically includes a crown portion 14 and 16, respectively, and a tubular hub 18 and 20, respectively.

As seen in FIG. 1, crown portion 14, which includes a clamping collar 22 and a series of five spirally shaped spring leaves 24, is attached to the left end of hub 18. Similarly, crown 16, which includes a clamping collar 26 and a series of five spirally shaped spring leaves 28 is secured to the right end of tubular hub 20, as seen in FIG. 1.

Each clamping collar 22 and 26 is in the form of a short cylindrical section of substantially larger diameter than its respective tubular hub 18 and 20 and is positioned coaxially about its respective hub spaced outwardly therefrom and centrally therealong. Spring leaves 24 and 28 are disposed at equal arcuate intervals about their respective hubs 18 and 20 at the ends thereof to which they are secured and extend radially and spirally to their respective clamping collars 22 and 26. Each series of spring leaves 24 and 28 thus forms a spiral latticework which permits the respective clamping collar 22 and 26 to be moved under the resilient biasing of spring leaves 24 and 26 axially toward the end of the respective hub 18 and 20 such that the spiral latice of spring leaves 24 and 26 forms a compression spring. By reason of the arcuate spacing of spring leaves 24 and 26, both about the end of hubs 18 an 20 and about clamping collars 22 and 26, the compressing stress is uniformly distributed about clamping collars 22 and 26.

Tubular hub 18 on clamping member 10 is open-ended and contains a medial tapped portion 30 which can be best seen in FIG. 3. Tubular portion 20 on clamping member 12 is also open-ended and has an outside diameter just less than the minor diameter of the threads in tapped portion 30 of hub 18. Hub 20, toward its left end as seen in FIG. 1, is provided with a pair of diametrically opposed U-shaped slots 32 which define a pair of leaves 34 formed of the wall section of hub 20 which are located near the left end of hub 20 and have their free ends extending toward the middle of hub 20. Leaves 34 carry pawls 36 near their free ends which extend outwardly above the outside wall of hub 20 and are positioned to engage the threads of tapped portion 30 of hub 18 when clamping members 10 and 12 are pushed together axially from the position shown in FIG. 1 to the position shown in FIG. 3. The engagement of pawls 36 with tapped portion 30 is that of a ratchet upon axial engagement of clamping members 10 and 12, but that of a threaded when disengaging the clamping halves by rotation. It will be noted particularly with reference to FIG. 3 that pawls 36 are offset lengthwise of hub 20 accommodate the half-turn of the threads in tapped portion 30 and thus assure that both pawls 36 will engage the threads of tapped portion 30 simultaneously, despite the diametrically opposed disposition of pawls 36.

As will be evident on viewing FIGS. 1 and 3, clamping members 10 and 12 are utilized in anastomosis of the cut ends of bowel sections $B_1$ and $B_2$, respectively, by positioning each clamping member 10 and 12 in the end of a bowel section $B_1$ and $B_2$ in a position such that the clamping rings 22 and 26 confront each other. The ends of bowel sections $B_1$ and $B_2$ are then pulled across the confronting edges of clamping rings 22 and 26, and clamping members 10 and 12 are then pushed toward each other with bowel section $B_1$ and $B_2$ firmly in position such that hub 20 has its left end as seen in FIG. 1 inserted into the right end of hub 18 to a point where the serosa of bowel sections $B_1$ and $B_2$ overlying the edges of clamping rings 22 and 26 are in contact.

At this point, the location of pawls 36 is such that they have engaged the threads on tapped portion 30. Clamping members 10 and 12 are then pushed closer toward each other to cause pawls 36 to move deeper into tapped portion 30. To facilitate this, leaves 34 bend inwardly to permit pawls 36 to pass the crests of the threads in portion 30 and then move outwardly to push pawls 36 into the troughs of the threads in the fashion of a ratchet. As clamping heads 10 and 12 are moved closer together, spring leaves 24 and 28 flex yieldingly to compress such that clamping rings 22 and 26 apply increasing pressure against each othr, pushing the serosa of bowel sections $B_1$ and $B_2$ into form contact.

It will be apparent that clamping members 10 and 12 should be made of material which will have the required physical properties to permit the necessary compression of spring leaves 24 and 28 and of spring leaves 34 and of sufficient stiffness such that substantial pressure can be generated between the confronting edges of clamping rings 22 and 26 when clampng members 10 and 12 are pushed together. A particularly suitable material is polyacetal resin which not only has the requisite physical properties but is relatively inert chemically, is non-toxic, and is amenable to adequate sterilization.

The device illustrated with reference to FIGS. 1-3 is particularly suitable for anastomosis of bowel sections of intermediate size and typically has an outside diameter of clamping rings 22 and 26 on the order of one inch, an outside diameter of hub portion 18 of one-half inch, an inside diameter of clamping rings 22 and 24 of seven-eighths of an inch, and an inside diameter of hub portion 20 of one-quarter inch.

In low lying rectal anastomosis, a nipple 38 can be threaded on to the end of clamping member 10 by engagement with tapped portion 30, and a flexible tube 40 can be attached to the nipple. The tube 40 can be made to protrude through the anus and can be connected to suction to ensure adequate decompression of the bowel in the region of the anastomosis.

Referring to FIG. 4, there is shown a modification for providing axial engagement of a pair of clamping members 50 and 52 which is particularly suitable for small diameter bowel sections.

Generally, clamping member 50 is constructed like clamping members 10, being provided with an open-ended tubular hub 54 having an internal tapped portion 56 and a crown including spiral spring leaves 58 and a clamping ring 60, which is positioned spaced outwardly of and coaxially along hub 54 by means of spring leaves 58. Clamping member 52 similarly has a hub 62, a clamping ring 64, which is positioned coaxially along hub 62 and spaced outwardly therefrom by means of spring leaves 66. However, because of the small diameters involved, hub 62 is solid rather than tubular, and supports a pair of pawls 68 for engagement with the tapped portion 56 on an elongated loop 70 which extends from hub 62 in a generally axial direction.

The use of the anastomosis button formed of clamping members 50 and 52 is generally the same as described with reference to clamping members 10 and 12.

In dealing with anastomosis of bowel sections of relatively large diameter, the positioning of the cut ends of the bowel section over the clamping rings of the clamping members is facilitated by the use of spreader rings 70 and 72 which is generally illustrated in FIGS. 5, 6, 7, and 8.

Figure 7:
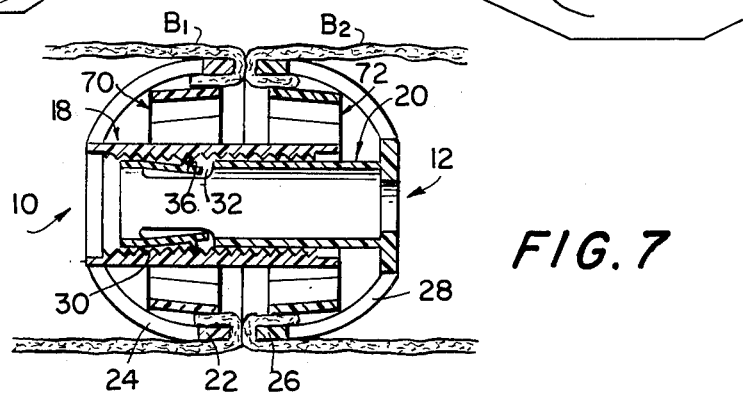
FIG. 7 is a view of the arrangement shown in FIGS. 5 and 6 which is similar to FIG. 3.
Figure 6:
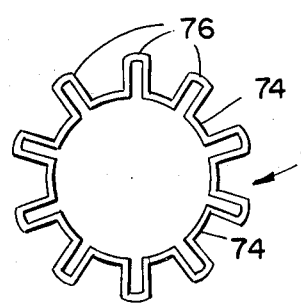
FIG. 6 is an end view of the added device.

Referring particularly to FIGS. 5 and 7, an anastomosis button is shown having clamping members essentially the same in construction as clamping members 10 and 12, except that the device is intended for larger diameter bowel sections and accordingly clamping members 10 and 12 are provided with six spring leaves each to support the clamping rings. For convenience in understanding, the same reference numerals have been used to designate the clamping members and their parts as were used with reference to FIGS. 1, 2, and 3. In this arrangement, however, there is added, associated with each clamping member 10 and 12, a bowel positioning element in the form of a spreader ring 70 and 72, respectively.

Each ring 70 and 72 is generally annular, corrugated radially and tapered lengthwise. Preferably, it is formed of a relatively flexible material, such as polyethylene. Referring more particularly to element 72, which is shown in elevation in FIG. 5, and in plan in FIG. 6, element 72 is a single piece of relatively thin wall section having an inner frustoconical wall 74 interrupted at arcuate intervals by radially outstanding corrugations 76. The inside cross dimension of element 72, approximating a minor diameter if it were cylindrical, is substantially larger than the outside diameter of axial hub 18. While the outside cross dimension, approximating the outside or major diameter of element 72 if it were cylindrical, is just less than the inside diameter of clamping rings 22 and 26.

Figure 8:
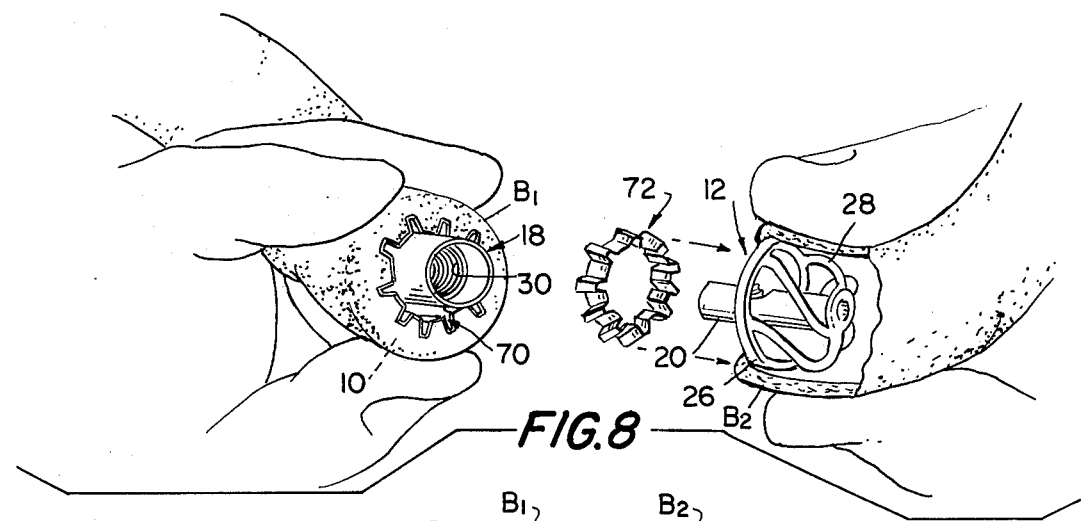
FIG. 8 is a perspective view illustrating joining the cut ends of the bowel using the devices of FIGS. 5, 6, and 7.

Spreader rings 70 and 72 are used in conjunction with clamping members 10 and 12, respectively to hold the cut ends of bowel sections to be joined firmly in position in each clamping member 10 and 12. Thus, referring to FIG. 8, for example, a bowel section $B_1$ has had a clamping member 10 positioned at its cut end, as described with reference to FIGS. 1-3. In addition, a spreader ring 70 has been pushed, leading with its tapered end, over hub 18 to force the ends of bowel section $B_1$ around clamping ring 22. As can be seen in FIG. 8, spreader ring 72 is similarly pushed into clamping member 12 over hub 20 to position the cut end of bowel section $B_2$ similarly over clamping ring 26. The two clamping members 10 and 12 are then pushed together as described above to bring the serosal surfaces of bowel sections $B_1$ and $B_2$ into firm contact. The use of spreader rings such as rings 70 and 72 is particularly desirable with larger diameter bowel sections, for example, on the order of an inch and a half, as the spreader rings aid in holding the inwardly turned ends of the bowel section out of the way to permit passage of fluids between the clamping rings and hubs of the anastomosis button clamping members.

I claim:

1. A clamping member for axial engagement with a complementary clamping member to form an anastomosis button, said clamping member including a hub and a crown, said hub including axial guiding and engaging means for axially mating and engaging a complementary hub on a said complementary clamping member, and said crown including a clamping collar coaxially positioned about and spaced radially outward of said hub medially located therealong and a plurality of resilient, flexible spring leaves spaced apart and attached at one set of ends thereof to said hub member at intervals thereabout to one side of said clamping collar, said leaves extending radially outward and lengthwise of said hub and said leaves being attached at the other set of ends thereof to said clamping collar at arcuate intervals thereabout.

2. A clamping member according to claim 1 in which said hub is an open-ended tube.

3. A clamping member according to claim 1 in which said plurality of spring leaves are spiral in form.

4. A clamping member according to claim 2 which further includes a flexible tube extending into said hub through the open end thereof and fastened therein.

5. A clamping member according to claim 1 for receiving a cut end of a bowel section positioned thereover and extended inwardly over said clamping collar, and a spreader ring positioned between said hub and said collar for outwardly pressing said cut end of said bowel section against the inner side of said collar.

6. The combination according to claim 5 in which said spreader ring is formed of relatively flexible material as a single piece of relatively thin wall section having an inner wall interrupted at arcuate intervals by radially outstanding corrugations.

* * * * *